US008697720B2

(12) United States Patent
Guiles et al.

(10) Patent No.: US 8,697,720 B2
(45) Date of Patent: *Apr. 15, 2014

(54) SUBSTITUTED PHENYLETHER-THIENOPYRIDONE COMPOUNDS WITH ANTIBACTERIAL ACTIVITY

(75) Inventors: Joseph Guiles, Lafayette, CO (US); Xicheng Sun, Superior, CO (US); Nebojsa Janjic, Boulder, CO (US); Sarah Strong, Louisville, CO (US)

(73) Assignee: Crestone, Inc., Boulder, CO (US)

( * ) Notice: Subject to any disclaimer, the term of this patent is extended or adjusted under 35 U.S.C. 154(b) by 1365 days.

This patent is subject to a terminal disclaimer.

(21) Appl. No.: 11/853,589

(22) Filed: Sep. 11, 2007

(65) Prior Publication Data
US 2008/0227808 A1 Sep. 18, 2008

Related U.S. Application Data

(60) Provisional application No. 60/826,954, filed on Sep. 26, 2006, provisional application No. 60/826,940, filed on Sep. 26, 2006, provisional application No. 60/826,945, filed on Sep. 26, 2006, provisional application No. 60/826,957, filed on Sep. 26, 2006.

(51) Int. Cl.
| A01N 43/42 | (2006.01) |
| A61K 31/44 | (2006.01) |
| C07D 513/02 | (2006.01) |
| C07D 515/02 | (2006.01) |
| C07D 215/00 | (2006.01) |

(52) U.S. Cl.
USPC ........... 514/301; 514/310; 514/312; 546/114; 546/153

(58) Field of Classification Search
USPC ................... 514/301, 310, 312; 546/114, 153
See application file for complete search history.

(56) References Cited

U.S. PATENT DOCUMENTS

| 4,710,506 | A | 12/1987 | Davies et al. |
| 6,943,175 | B2 | 9/2005 | Berge et al. |
| 7,030,137 | B2 | 4/2006 | Berge et al. |
| 7,220,757 | B2 | 5/2007 | Berge et al. |
| 7,973,050 | B2 | 7/2011 | Guiles et al. |
| 7,994,192 | B2 | 8/2011 | Guiles et al. |
| 2008/0108651 | A1 | 5/2008 | Guiles et al. |
| 2008/0146609 | A1 | 6/2008 | Guiles et al. |
| 2009/0163536 | A1 | 6/2009 | Guiles et al. |

FOREIGN PATENT DOCUMENTS

| EP | 0785268 | 7/1997 |
| WO | WO 99/55677 | 11/1999 |
| WO | WO 00/21949 | 4/2000 |
| WO | WO 00/71524 | * 11/2000 |
| WO | WO 2004/052288 | 6/2004 |
| WO | WO 2004/069196 | 8/2004 |
| WO | WO 2004/078119 | 9/2004 |
| WO | WO 2008/039639 | 4/2008 |
| WO | WO 2008/039640 | 4/2008 |
| WO | WO 2008/039641 | 4/2008 |
| WO | WO 2008/039642 | 4/2008 |

OTHER PUBLICATIONS

U.S. Appl. No. 11/853,314, filed Sep. 11, 2007, Guiles et al.
Bartlett & Perl, (2005) N. Engl. J Med. 353:2503-2505.
Clabots et al. (1992) J Infect. Dis. 166:561-567.
Fleischmann et al. (1995) Science 269:496-512.
Jarvest et al. (2004) Bioorg. & Med. Chem. Lett. 14:3937-3941.
McFarland et al. (1989) N. Engl. J Med. 320:204-210.
Bartlett et al (1978) "Role of *Clostridium difficile* in Antibiotic-Associated *Pseudomembranous colitis*" Gastroenterology 75(5):778-782.
Critchley et al (2005) "Antibacterial Activity of REP8839, a New Antibiotic for Topical Use" Antimicrobial Agents and Chemotherapy 49(10):4247-4252.
EP Supplemental Search Report (Mar. 21, 2011) received in EP Application No. 07842226.8.
Gentry et al (2003) "Variable Sensitivity to Bacterial Methionyl-tRNA Synthetase inhibitors Reveals Subpopulations of *Streptococcus pneumoniae* with Two Distinct methionyl-tRNA Synthetase Genes" Antimicrobial Agents and Chemotherapy 47(6):1784-1789.
Hall and O'Toole (1935) "Intestinal Flora in Newborn Infants with Description of a New Pathogenic Anaerobe" American Journal of Diseases of Children 49:390-402.
Jarvest et al (2002) "Nanomolar Inhibitors of *Staphylococcus aureus* Methionyl tRNA Synthetase with Potent Antibacterial Activity Against Gram-Positive Pathogens" Journal of Medicinal Chemistry 45(10):1959-1962.
Loo et al (2005) "A Predominantly Clonal Multi-Institutional Outbreak of *Clostridium difficile*—Associated Diarrhea with High Morbidity and Mortality" New England Journal of Medicine 353:2442-2449.
Lyerly et al (1988) "*Clostridium difficile*: Its Disease and Toxins" Clinical Microbiology Reviews 1(1):1-18.
Pépin et al (2005) "Increasing Risk of Relapse After Treatment of *Clostridium difficile* Colitis in Quebec, Canada" Clin. Infect. Dis. 40:1591-1597.
Teasley et al (1983) "Prospective Randomised Trial of Metronidazole Versus Vancomycin for *Clostridium-difficile*-Associated Diarrhoea and Colitis" The Lancet 2:1043-1046.
Thomas et al (2003) "Antibiotics and Hospital-Acquired *Clostridium difficile*-Associated Diarrhoea: a Systematic Review" Journal of Antimicrobial Chemotherapy 51:1339-1350.

(Continued)

*Primary Examiner* — Sreeni Padmanabhan
*Assistant Examiner* — Uma Ramachandran
(74) *Attorney, Agent, or Firm* — Swanson & Bratschun, LLC

(57) ABSTRACT

Novel bicyclic heteroaromatic compounds are provided that are inhibitors of bacterial methionyl tRNA synthetase (MetRS). Compounds of the invention generally have a left hand side phenylether constituent and a right hand side thienopyridone constituent. Also disclosed are methods for their preparation and their use in therapy as antibacterial agents, particularly as anti-*Clostridium difficile* agents.

7 Claims, No Drawings

(56) References Cited

OTHER PUBLICATIONS

Voth and Ballard (2005) "*Clostridium-difficile* Toxins: Mechanism of Action and Role in Disease" Clinical Microbiology Reviews 18(2):247-163.

Wilcox and Spencer (1992) "*Clostridium difficile* Infection: Responses, Relapses and Re-Infections" Journal of Hospital Infection 22:85-92.

Barker (1995) "An Easy Synthesis of 3-Amino- and 3-Nitrothiophene" Synthetic Comm 25:3729-3734.

Brown et al (2003) "Horizontal Transfer of Drug-Resistant Aminoacyl-Transfer-RNA Synthesis of Anthrax and Gram-Positive Pathogens" EMBO Reports 4(7):692-698.

Elsayed and Zhang (2004) "Bacteremia Caused by *Clostrididum symbiosum*" J. Clin. Microbiology 42(9):4390-4392.

Hurdle et al (2005) "Prospects for Aminoacyl-tRNA Synthetase Inhibitors as New Antimicrobial Agents" Antimicrobial Agents and Chemotherapy 49(12):4821-4833.

Jarvest et al (2003) "Conformational Restriction of Methionyl tRNA Synthetase Inhibitors Leading to Analogues with Potent Inhibition and Excellent Gram-Positive Antibacterial Activity" Bioorganic & Medicinal Chemistry Letters 13:1265-126.

Jiang et al (2009) "*Clostridium glycolicum* Wound Infections: Case Reports and Review of the Literature" J. Clin. Microbiology 47(5):1599-160.

Kim and Lee (2003) "3-D-QSAR Study and Molecular Docking of Methionyl-tRNA Synthetase Inhibitors" Bioorganic & Medicinal Chemistry 11:5325-533.

King (1994) "Bioisosteres, Conformational Restriction, and Prodrugs-Case History: An Example of a Conformational Restriction Approach" Medicinal Chemistry: Principle and Practice:206-22.

Lin et al (2001) "Principles and Applications of Asymmetric Synthesis" Wiley-Interscience pp. 1-1.

Office Action mailed Nov. 24, 2010 with respect to U.S. Appl. No. 11/853,636.

Office Action mailed Sep. 23, 2010 with respect to U.S. Appl. No. 11/853,477.

Office Action mailed Sep. 15, 2010 with respect to U.S. Appl. No. 11/853,314.

Smith M.B., (2001) "The Cahn-Ingold-Prelog System" March J, March's Advanced Org. Chem., 5th ed., Wiley-Interscience, NY, p. 139-143.

Smith-Slatas et al (Mar. 27, 2006) "*Clostridium septicum* Infections in Children: A Case Report and Review of the Literature" Pediatrics 117:e796-e805 (http:www.pediatrics.org/cgi/content/full/117/4/e796).

Notice of Allowance mailed May 13, 2011 with respect to U.S. Appl. No. 11/853,477.

Notice of Allowance mailed May 18, 2011 with respect to U.S. Appl. No. 11/853,314.

\* cited by examiner

SUBSTITUTED PHENYLETHER-THIENOPYRIDONE COMPOUNDS WITH ANTIBACTERIAL ACTIVITY

RELATED APPLICATIONS

This application claims the benefit under 35 U.S.C. §119, of U.S. Provisional Patent Application Ser. No. 60/826,954 entitled SUBSTITUTED PHENYLETHER-THIENOPYRIDONE COMPOUNDS WITH ANTIBACTERIAL ACTIVITY, filed Sep. 26, 2006, and incorporated by reference herein in its entirety. This application also claims the priority benefit of U.S. Patent Applications: ENANTIOMERIC COMPOUNDS WITH ANTIBACTERIAL ACTIVITY, Ser. No. 60/826,940, filed Sep. 26, 2006; SUBSTITUTED THIENOPYRIDONE COMPOUNDS WITH ANTIBACTERIAL ACTIVITY, Ser. No. 60/826,945 filed Sep. 26, 2006; and METHODS AND COMPOUNDS FOR TREATMENT OF *CLOSTRIDIUM* BASED INFECTION, Ser. No. 60/826,957 filed Sep. 26, 2006. The current application is also related to U.S. Pat. No. 6,943,175, filed Dec. 5, 2003, and U.S. Pat. No. 7,030,137, filed Feb. 27, 2004, and to U.S. patent application Ser. No. 10/729,416, filed Dec. 5, 2003 and Ser. No. 11/223,327, filed Sep. 9, 2005. Each of the above referenced applications and patent is incorporated by reference herein for all purposes.

TECHNICAL FIELD

The present invention relates to novel bicyclic heteroaromatic compounds having a left hand side phenylether and right hand side thienopyridone, and in particular to the use of these compounds as inhibitors of bacterial methionyl tRNA synthetases (MetRS), to processes for their preparation and to their uses in therapy as antibacterial agents, and in particular to their uses in therapy of *Clostridium difficile* based infections.

BACKGROUND OF THE INVENTION

The search for antibacterial agents began in the late 1800s with the realization that "germs" caused human disease. Over the past century scientists have developed a variety of drugs useful in the targeting and inhibition of numerous bacterial strains. In particular, antibacterial agents known as antibiotics have been developed and are in common use throughout the industrialized world to treat most known bacterial infections. Originally, antibiotics like penicillin inhibited replication of bacteria by blocking the action of transpeptidase, an enzyme responsible for the building of bacterial cell walls. However, due to overuse and resistance adaptations of many bacterial strains, many antibiotics have lost some or all of their effectiveness at treating infection. A line of antibacterial agents that target new molecular growth mechanisms would be useful in avoidance of further enhancement of antibiotic resistance. One such target is t-RNA synthetase.

tRNA synthetases are involved in protein biosynthesis so that inhibition thereof may be expected to lead to a cessation of cell growth. Thus, for instance, the compound mupirocin, produced by the organism *Pseudomonas fluorescens*, is an antibacterial agent and is used as the active ingredient in the product Bactroban®, marketed by GlaxoSmithKline. Mupirocin has been shown to be an inhibitor of the isoleucyl tRNA synthetase. Each tRNA synthetase represents a separate target for drug discovery. tRNA synthetase inhibitors which are selective for bacterial cells over mammalian cells are of considerable therapeutic interest as they have the potential to be used as antibacterial agents.

The sequence of the tRNA synthetase genes in the Gram positive organism *S. aureus* have recently been determined (see, for instance, European Patent application no 97300317.1, SmithKline Beecham, for *S. aureus* MetRS), thereby assisting the process of identifying inhibitors. In addition, the sequence of tRNA synthetase genes in other pathogenic bacteria, for instance the Gram negative organism *H. influenzae*, has also been published (R. D. Fleischmann et al., Science, 269, 496-512, 1995).

Several compounds have recently been disclosed for their inhibitory activity toward methionyl tRNA synthetase (MetRS) and for their capacity as antibacterial agents. In particular, Jarvest et al. described various bicyclic heteroaromatic compounds that have shown MetRS inhibition. (Bioorg. & Med. Chem. Lett. 14 (2004) 3937-3941). There is a need in the art to continue to identify and utilize compounds that target MetRS and thereby provide new approaches for the treatment of bacterial infection.

One particularly interesting bacterial target is the organism *Clostridium difficile* (*C. difficile*). *C. difficile* is becoming a more prevalent infectious agent, where one to three percent of healthy individuals are carriers of the organism. (Bartlett & Perl, N. Engl. J. Med., 353, 2503-2505, 2005; Clabots et al., J. Infect. Dis., 166, 561-567, 1992; McFarland et al., N. Engl. J. Med., 320, 204-210, 1989). The risk of infection and disease becomes increasingly prevalent in the immunodeficient, elderly, and especially to the elderly in healthcare settings, e.g., nursing home, hospital, doctors office, etc. Few conventional antibacterial drugs have shown promise in the treatment of *C. difficile*, in fact only vancomycin is approved by the FDA for treatment of *C. difficile* associated diarrhea (CDAD). As such, there is a need in the art to obtain additional approaches for the treatment of *C. difficile* based infection, especially treatments that avoid conventional antibiotic treatments and therefore antibiotic resistance.

Against this backdrop the present invention has been discovered.

DETAILED DESCRIPTION OF THE INVENTION

We have now found a novel class of bicyclic heteroaromatic compounds that are potent inhibitors of bacterial MetRS. This new class of compounds is shown to have broad applicability as antibacterial agents for numerous Gram-positive and Gram-negative bacteria. MetRS inhibitors of the invention have superior activity against Gram-positive organisms, in particular *C. difficile*, as compared to Gram-negative organisms.

In general, bicyclic heteroaromatic compounds of the invention have a left hand side (LHS) phenylether and a right hand side (RHS) thienopyridone.

In particular, the invention provides compounds of the formula (I):

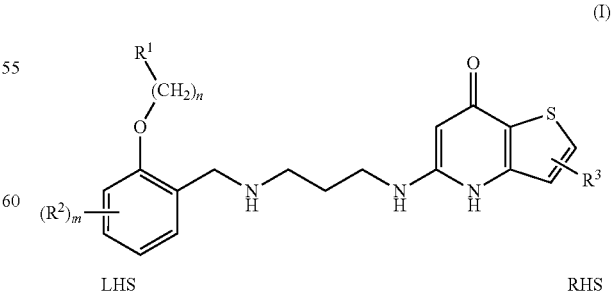

in which $R^1$ is selected from the group consisting of aryl and heteroaryl groups, including but not limited to substituted and unsubstituted benzene, toluene, phenol, anisole, thiazole, thiazolidine and pyridine, alkenes, imines, and other like substituents;

$R^2$ is independently selected from halo, cyano, hydroxyl, $(C_{1-6})$alkyl (optionally substituted by halo, hydroxyl, amino, carboxy, or $(C_{1-6})$ alkoxycarbonyl), $(C_{1-6})$ cycloalkyl, $(C_{1-6})$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heteroxy;

$R^3$ is selected from a halo, $(C_{1-3})$alkyl, $(C_{2-3})$alkenyl, $(C_{2-3})$alkynyl or other like substituents;

n is one, two or three; and m is 0, 1, 2 or 3.

The preferred embodiments of the invention are those compounds of formula (IA):

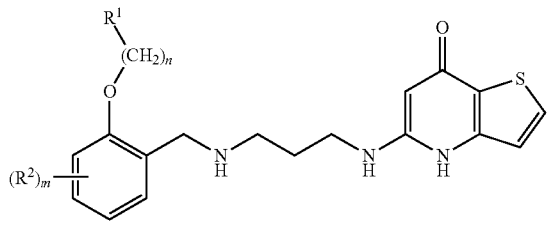

(IA)

in which:

$R^1$ is selected from the group consisting of substituted and unsubstituted benzene, such as toluene, phenol, anisole, substituted and unsubstituted thiazole, such as methylthiazole, substituted and unsubstituted pyridine, and alkenyl groups ethanimine, and $(C_1-C_6)$alkene;

$R^2$ is one or more halogen substituents (preferably bromine, iodine and/or chlorine), one or more sulfane substituents, e.g., methylsulfane, or a combination of a halogen and sulfane substituents;

n is one, two or three; and m is 0, 1, 2, or 3.

Compounds of formula (I) and (IA) are novel inhibitors of bacterial MetRS but show limited activity toward mammalian MetRS.

Salts may be formed from inorganic and organic acids. Representative examples of suitable inorganic and organic acids from which pharmaceutically acceptable salts of compounds of formula (I) or formula (IA) may be formed include maleic, fumaric, benzoic, ascorbic, pamoic, succinic, bismethylene-salicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms "alkenyl" and "alkynyl" include all straight chain and branched isomers. Representative examples thereof include vinyl, ethynyl and 1-propynyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$ alkoxy, halo$(C_{1-6})$alkyl, hydroxy, amino, mono- or di-$(C_{1-6})$ alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$ alkyl, carboxy$(C_{1-6})$alkyl, $(C_{1-6})$alkylcarbonyloxy, carboxy $(C_{1-6})$alkyloxy, $(C_{1-6})$alkoxycarbonyl$(C_{1-6})$alkoxy, $(C_{1-6})$ alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred substituents include those previously mentioned for an aryl group as well as oxo.

When used herein, the terms "halogen" and "halo" include fluorine, chlorine, bromine, and iodine and fluoro, chloro, bromo, and iodo, respectively.

The compounds of the present invention are suitably provided in substantially pure form, for example at least 50% pure, suitably at least 60% pure, advantageously at least 75% pure, preferably at least 85% pure, more preferably at least 95% pure, especially at least 98% pure. All percentages are calculated on a weight/weight basis. All impure or less pure forms of a compound according to the invention may, for example, be used in the preparation of more pure forms of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. Embodiments of the invention cover all such stereoisomers, and mixtures thereof, including racemates and mixtures having an enantiomeric excess of one of the enantiomers.

Accordingly, the present invention provides preferred compounds of the formulas (II)-(XV):

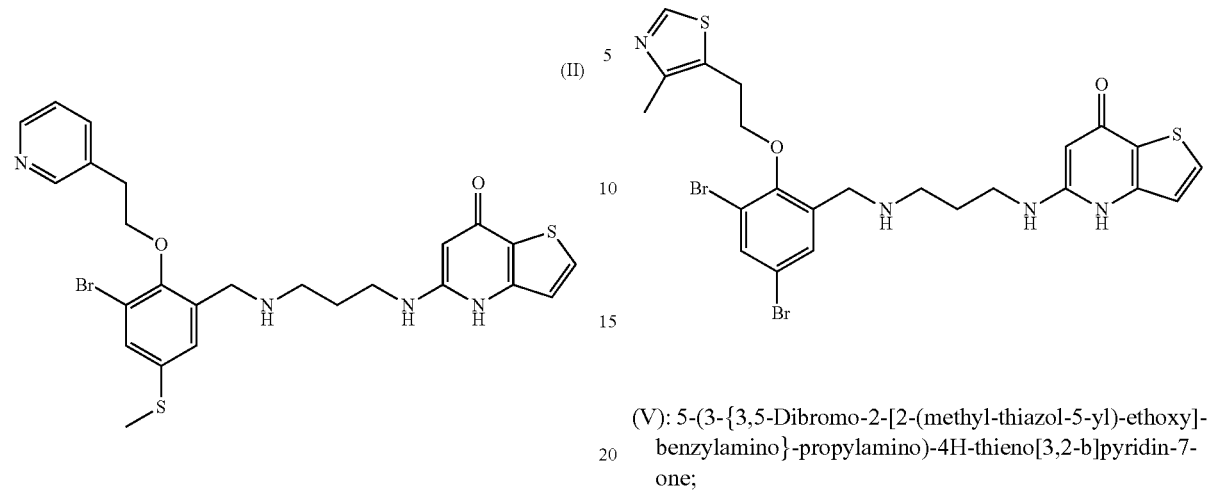

(II): 5-{3-[3-Bromo-5-methylsulfanyl-2-(2-pyridin-3-yl-ethoxy)-benzylamino]-propylamino}-4H-thieno[3,2-b]pyridin-7-one;

(III): 5-(3-{3-bromo-5-methylsulfanyl-2-[2-(4-methyl-thiazol-5-yl)-ethoxy]-benzylamino}-propylamino)-4H-thieno[3,2-b]pyridin-7-one;

(IV): 5-[3-(3-bromo-5-methylsulfanyl-2-phenethyloxy-benzylamino)-propylamino]-4H-thieno[3,2-b]pyridin-7-one;

(V): 5-(3-{3,5-Dibromo-2-[2-(methyl-thiazol-5-yl)-ethoxy]-benzylamino}-propylamino)-4H-thieno[3,2-b]pyridin-7-one;

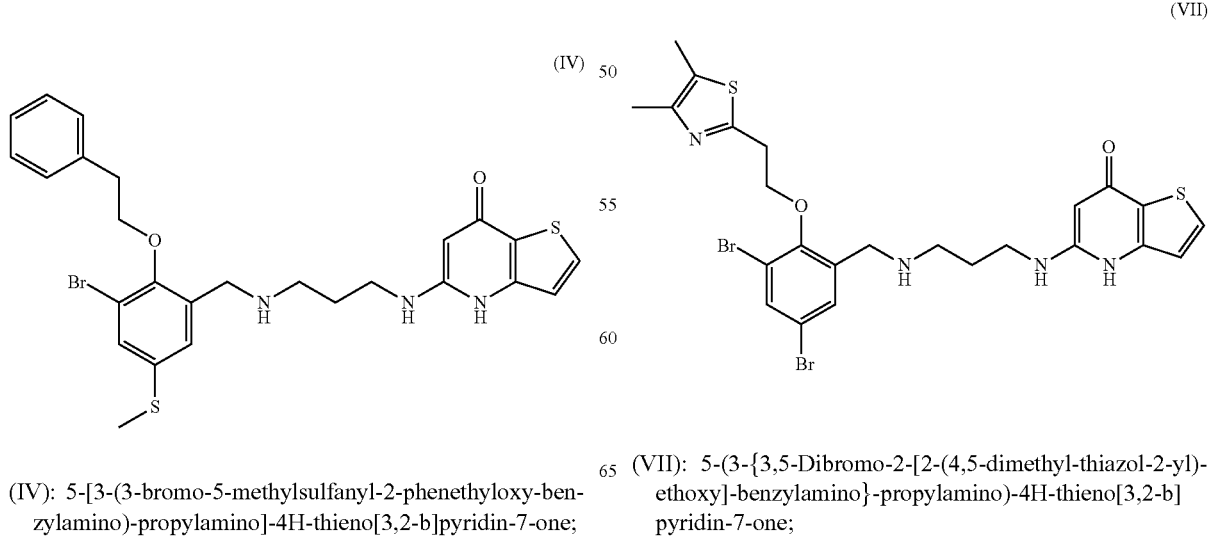

(VI): 5-{3-[3,5-Dibromo-2-(2-pyridin-3-yl-ethoxy)-benzylamino]-propylamino}-4H-thieno[3,2-b]pyridin-7-one;

(VII): 5-(3-{3,5-Dibromo-2-[2-(4,5-dimethyl-thiazol-2-yl)-ethoxy]-benzylamino}-propylamino)-4H-thieno[3,2-b]pyridin-7-one;

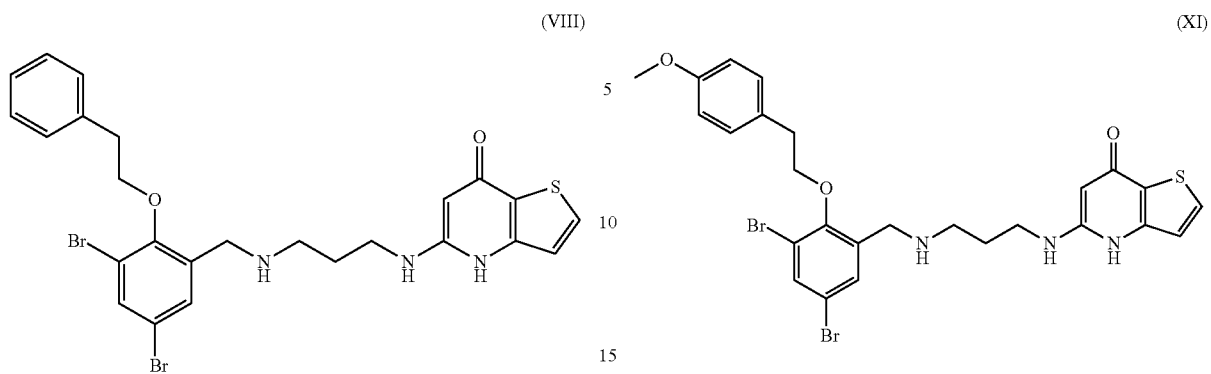

(VIII): 5-[3-(3,5-Dibromo-2-phenethyloxy-benzylamino)-propylamino]-4H-thieno[3,2-b]pyridin-7-one;

(XI): 5-(3-{3,5-Dibromo-2-[2-(4-methoxy-phenyl)-ethoxy]-benzylamino}-propylamino)-4H-thieno[3,2-b]pyridin-7-one;

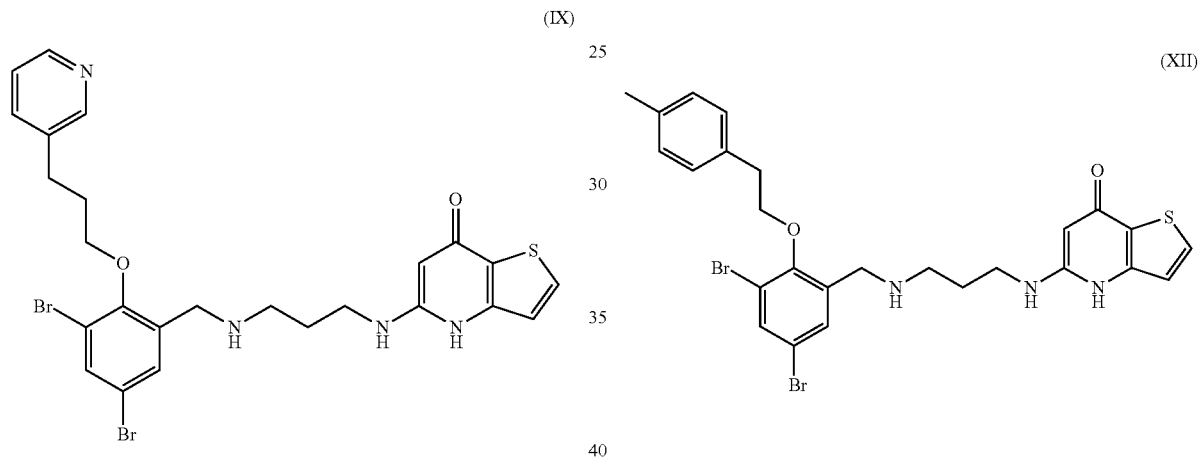

(IX): 5-{3-[3,5-Dibromo-2-(3-pyridin-3-yl-propoxy)-benzylamino]-propylamino}-4H-thieno[3,2-b]pyridin-7-one;

(XII): 5-{3-[3,5-Dibromo-2-(2-p-tolyl-ethoxy)-benzylamino]-propylamino}-4H-thieno[3,2-b]pyridin-7-one;

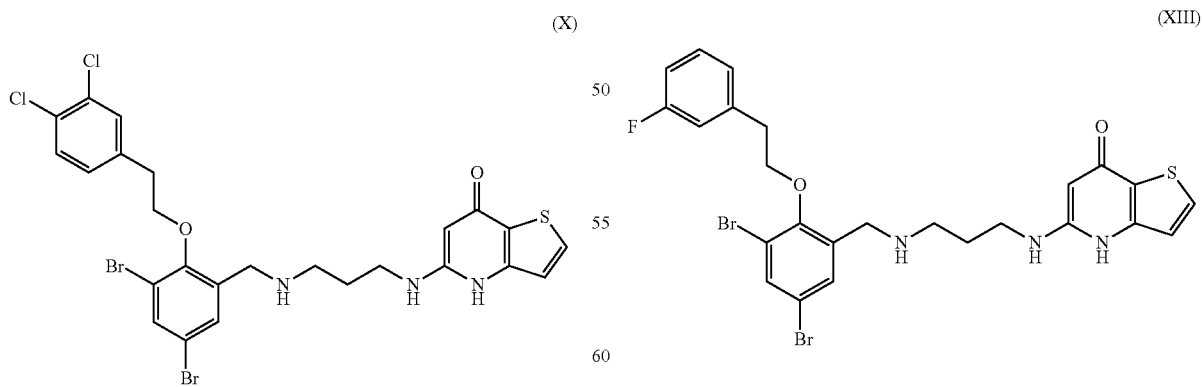

(X): 5-(3-{3,5-Dibromo-2-[[2-(3,4-dichloro-phenyl)-ethoxy]-benzylamino}-propylamino)-4H-thieno[3,2-b]pyridin-7-one;

(XIII): 5-(3-{3,5-Dibromo-2-[2-(3-fluoro-phenyl)-ethoxy]-benzylamino}-propylamino)-4H-thieno[3,2-b]pyridin-7-one;

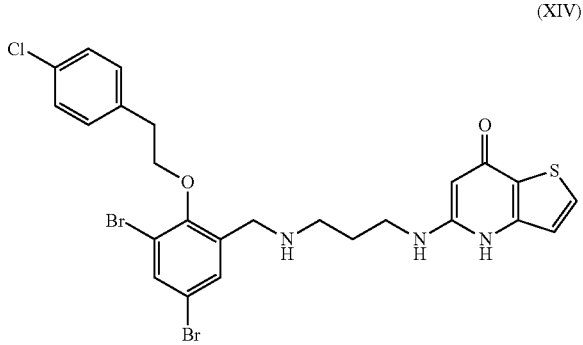 [SMILES: O=c1cc(NCCCNCc2cc(Br)cc(Br)c2OCCc2ccc(Cl)cc2)[nH]c2ccsc12]

(XIV): 5-(3-{3,5-Dibromo-2-[2-(4-chloro-phenyl)-ethoxy]-benzylamino}-propylamino)-4H-thieno[3,2-b]pyridin-7-one; and

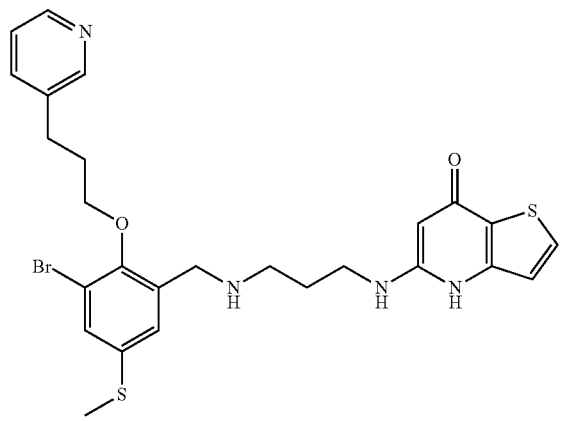

(XV): 5-{3-[3-Bromo-5-methylsulfanyl-2-(3-pyridin-3-yl-propoxy)-benzylamino]-propylamino}-4H-thieno[3,2-b]pyridin-7-one.

The compounds of formula (I)-(XV) may be prepared by methods described herein (see Example 1) or by methods described in the prior art that are incorporated by reference herein below.

For example, a compound of formula (I) is generally prepared by reductive amination of 5-(3-aminopropylamino) thieno[3,2-b]pyridin-7-one (formula XVIII) with a substituted phenylether aldehyde (formula XVII) (see Example 1, Synthesis Scheme 1).

The compounds of this invention are active against a range of important pathogenic bacteria, including Gram positive organisms, such as Staphylococci, for instance *S. aureus* Oxford and coagulase negative strains of Staphylococci such as *S. epidermidis*; Streptococci, for instance *S. pyogenes* ATCC19615 and *S. pneumoniae* R6; *Clostridium*, for instance *C. difficile*, and Enterococci, for instance *E. faecalis* 1 and *E. faecium*. Preferably, compounds of this invention are also active against gram negative organisms, such as *Haemophilus*, for instance *H. influenzae* Q1; *Moraxella*, for instance *M. catarrhalis* 1502; *Escherichia*, for instance *E. coli* DC0; and *Helicobacter*, for instance *H. pylori* ATCC 700824. The most preferred compounds of the present invention will be active against the organisms *C. difficile, S. aureus, S. pneumoniae, E. faecalis, E. faecium, H. influenzae, M. catarrhalis*, and *H. pylori*.

In addition, compounds of this invention are active against Staphylococci organisms such as *S. aureus* and coagulase negative strains of Staphylococci such as *S. epidermidis* which are resistant (including multiply-resistant) to other antibacterial agents, for instance, β-lactam antibiotics such as, for example, methicillin, macrolides, aminoglycosides, oxazolidinones, and lincosamides.

Compounds of the present invention are also active against strains of *E. faecalis* including vancomycin resistant strains and therefore of use in treating infections associated with VRE organisms. Furthermore, compounds of the present invention are useful in the treatment of Staphylococci organisms which are resistant to mupirocin.

Compounds of the present invention have particularly potent activity against strains of *Clostridium* including *C. difficile*. Therefore, compounds of the invention can be used to treat infections associated with *C. difficile*, e.g., pseudomembraneous colitis, toxic megacolin, and other antibiotic associated diarrheas (AAD).

Compounds of the present invention show little or no activity against mammalian cells. This provides an optimal combination of high activity against pathogenic bacteria and low or no activity against mammalian cells, allowing for the use of the compounds of the invention in human treatments.

Bacterial infections which may be treated include gastrointestinal tract infections, respiratory tract infections, otitis media, meningitis, endocarditis, skin and soft tissue infections in man, mastitis in cattle, and also respiratory infections in farm animals such as pigs and cattle. Accordingly, in a further aspect, the present invention provides a method of treating bacterial infection in human or non-human animals, which method comprises administering a therapeutically effective amount of a compound of formula (I)-(XV) as hereinbefore defined, to a human or non-human animal in need of such therapy. It will be appreciated that a compound of the present invention which has a broad spectrum of antibacterial activity, including activity against both Gram positive and Gram negative bacteria will be of general use in the community for the empiric treatment of community acquired infections. In comparison, a compound of the present invention with a more limited spectrum, for instance activity against Gram positive bacteria, is more likely to be used in circumstances where the causative pathogenic organism has been identified.

The present invention provides a pharmaceutical composition comprising a compound of formula (I)-(XV) together with a pharmaceutically acceptable carrier or excipient.

The present invention further provides pharmaceutical compositions comprising combinations of compounds of formula (I)-(XV) together with a pharmaceutically acceptable carrier or excipient. For example, a pharmaceutical composition of the invention can include a compound of formula (III) and a compound of formula (VI) in combination with the carrier or excipient.

The present invention also provides a method of treating bacterial infections in mammals, especially in humans and in domesticated animals, which comprises administering a compound of the invention, or a composition according to the invention, to a patient in need thereof.

The invention further provides the use of compounds of the invention in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical, parenteral, or rectal. The compositions may, for example, be made up in the form of tablets, capsules, powders, granules, lozenges, creams, suppositories, ointments, gels, lotions, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sucrose, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavoring and color agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, and solvents to assist drug penetration, and emollients in ointments, gels, and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilized before being filled into a suitable vial or ampoule, which is then sealed. Advantageously, conventional additives including, for example, local anesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilization cannot be accomplished by filtration. The compound may instead be sterilized by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration. Note that where a composition includes two or more compounds of the invention, the total weight/weight of the inhibitors is equal to from 0.1% to about 60%, i.e., compound (II) contributes 2% and compound (III) contributes 2% for a total of 4%.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 40 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compound according to the invention.

Examples 20-24 below illustrate the potent antibacterial activity of the compounds of the present invention. In particular, Example 21, 23 and 24 illustrate the surprisingly potent antibacterial activity of compounds of the invention against *C. difficile*, an organism that has proven to be difficult to treat using conventional antibiotic therapies.

EXAMPLES

The following examples are provided for illustrative purposes only and are not intended to limit the scope of the invention.

Example 1

Synthesis Schemes for Preparation of Compounds of the Present Invention

Synthetic Scheme I:

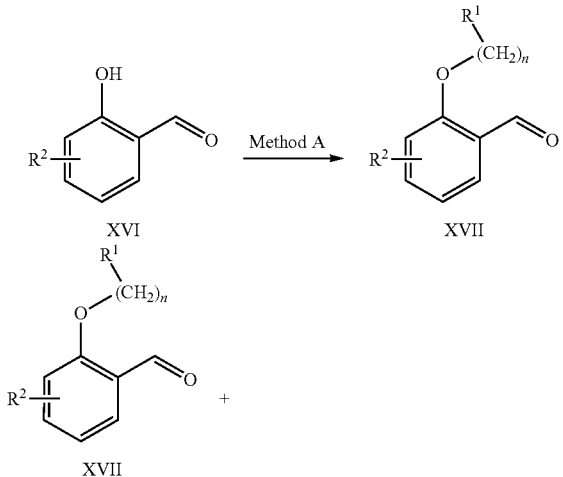

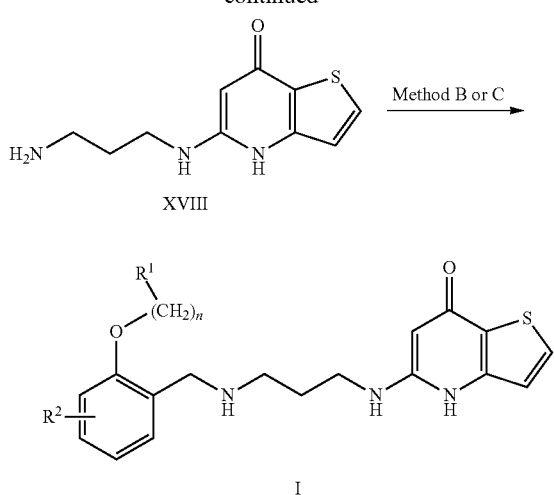

Synthetic Scheme II:

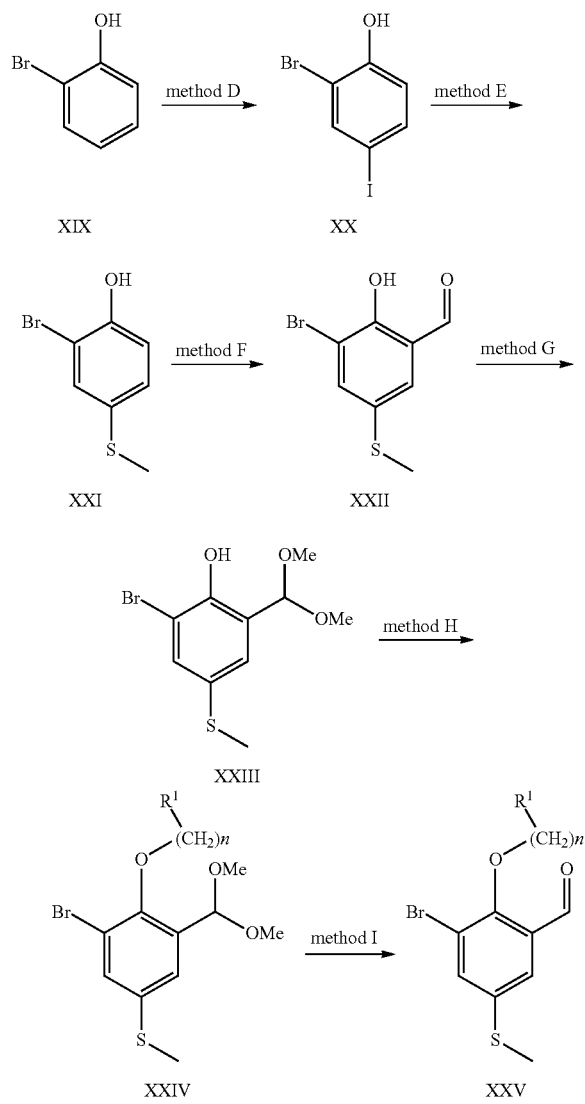

Method A: Preparation of Compound XVII

2-Bromophenol (XVI) was dissolved in DMF and $K_2CO_3$ (1.0 equivalent) was added. In a separate vessel, the $R^1$ containing alcohol reagent was converted to its mesolate by dissolving the alcohol (1.0 equivalent) in DMF at 0° C. and treating with methanesulfonyl chloride (1.0 equivalent) and Hunig's base (1.0 equivalent). This solution was kept at 0° C. and was added to the 2-bromophenol solution above. The reaction mixture was then heated to 50° C. and stirred at this temperature for 3 days. The reaction mixture was filtered and washed with THF. The combined filtrate was concentrated and the residue purified by silica gel column chromatography using ethyl acetate/hexanes gradient to afford compound (XVII).

Method B: Reductive Amination

The aldehyde (XVII) was dissolved in methanol and sodium methoxide (2.0 equivalents) was added, the HCl salt of compound XVIII (prepared according to methods described in U.S. patent application Ser. No. 11/853,314, entitled "Substituted Thienopyridone Compounds with Antibacterial Activity," filed Sep. 11, 2007) and acetic acid were then added to the mixture. The reaction was stirred at ambient temperature for 2 hours. The solvent was removed by evaporation and dichloromethane was added to the residue. Sodium triacetoxyborohydride (2.5 equivalents) was added and the reaction was stirred at ambient temperature overnight. Purification of the crude product was accomplished by flash chromatography, eluting the product with a gradient between dichloromethane and saturated ammonia in MeOH (up to 15%). The resulting solid was triturated with ether, isolated by filtration, and dried to give the title compound (I) as a white solid.

Method C: Reductive Amination

A solution of 5-(3-amino-propylamino)-4H-thieno[3,2-b]pyridine-7-one hydrochloride salt (compound XVIII, 1.2 equivalents) in methanol was treated with 2N NaOH (2.4 equivalents). The benzaldehyde (compound XVII, 1.0 equivalent) in THF was added to the reaction mixture. The resultant solution was stirred 2 to 4 hours, followed by treatment with $NaBH_4$ (1.2 equivalents). The reaction mixture was stirred 1 to 2 hours and diluted with EtOAc and water. The layers were separated and the organic was partitioned with brine and then dried with anhydrous $MgSO_4$, filtered and solvent removed in vacuo. The resulting residue was purified by silica gel column chromatography, eluting the product with a gradient between dichloromethane and saturated ammonia in MeOH (up to 15%) to give the title compound (I).

Method D: Preparation of 2-bromo-4-iodophenol (XX)

Sodium iodide (14.2 g) and sodium hydroxide (3.8 g) were added to a solution of 2-bromophenol (XIX, 16.4 g) in methanol (250 mL). The resultant solution was chilled to 0° C. A commercial bleach solution (6% NaClO, 120 mL) was added drop wise at 0-3° C. over 2 h. After the addition, the reaction mixture was stirred for 1 h at 5° C., then treated with 10% sodium thiosulfate aqueous solution (100 mL) and acidified with concentrated HCl to pH 5-7. The mixture was extracted with EtOAc (150 mL×3). The combined organic layers were partitioned with brine, dried over $MgSO_4$, filtered and concentrated under reduced pressure. The resultant oil was purified by silica gel column chromatography; the product eluted with dichloromethane/hexane (2:3), to afford the desired product as a colorless solid (14.76 g, 52%).

$^1$H NMR (400 MHz, CDCl$_3$) δ 7.72 (1H, s), 7.49 (1H, d), 6.78 (1H, d), 5.48 (1H, s). LC-MS (ES, E$^-$): found 297 (M–H)$^-$ and 299 (M–H)$^-$, as calculated: 298 for C$_6$H$_4$$^{79}$BrIO and 300 for C$_6$H$_4$$^{81}$BrIO.

Method E: Preparation of 2-bromo-4-methylsulfanylphenol (XXI)

Sodium thiomethoxide (8.64 g) and copper (I) oxide (8.79 g) were mixed with 2-bromo-4-iodophenol (XX, 14.72 g) in anhydrous DMF (100 mL). The mixture was stirred and heated at 80° C. for 48 h under nitrogen atmosphere. Then, the resultant slurry was treated with concentrated HCl (5 mL) and EtOAc (200 mL), and was filtered and rinsed with EtOAc (200 mL). The organic layers were partitioned with 1N HCl (150 mL), water (150 mL) and brine (150 mL) and dried over MgSO$_4$, filtered and solvent removed in vacuo. Product was purified by silica gel column chromatography, the product eluted with dichloromethane/hexane (2:3), to give the desired product (5.22 g, 39%) as a light brown oil.

$^1$H NMR (400 MHz, CDCl$_3$) δ 7.42 (1H, s), 7.19 (1H, d), 6.95 (1H, d), 5.40 (1H, s), 2.41 (3H, s).

Method F: Preparation of 3-bromo-2-hydroxyl-5-methylsulfanylbenzaldehyde (XXII)

Anhydrous paraformaldehyde (2.14 g) and anhydrous magnesium chloride (–10 mesh, 99.9%, 4.53 g) were suspended in anhydrous THF (120 mL) under nitrogen atmosphere. Freshly distilled TEA (6.7 mL) was added to the above suspended solution and stirred for 30 minutes. To the above mixture, a solution of 2-bromo-4-methylthiophenol (XXI, 5.22 g) in anhydrous THF (40 mL) was added. The resultant mixture was heated at gentle reflux and stirred for 6 h. After the mixture was cooled down to ambient temperature, ether (100 ml) was added. The organic layer was washed with 1N HCl (60 mL×3) and water (60 mL×3), and dried over MgSO$_4$, filtered and solvent removed in vacuo. The mixture was recrystallized from hexane to afford the product (3.60 g, 61%) as a yellow solid.

$^1$HNMR (400 MHz, CDCl$_3$) δ 11.44 (1H, s), 9.84 (1H, s), 7.76 (1H, s), 7.49 (1H, s), 2.50 (1H, s). LC-MS (ES, E$^-$): found 245 (M–H)$^-$ and 247 (M–H)$^-$, as calculated: 246 for C$_8$H$_7$$^{79}$BrO$_2$S and 248 for C$_8$H$_7$$^{81}$BrO$_2$S.

Method G: General Procedure to Prepare Protected Aldehyde (XXIII)

3-Bromo-2-hydroxyl-5-methylsulfanyl benzaldehyde (XXII, 1.0 equivalent, e.g. 17.4 mmol) was dissolved in methanol (20 mL) and trimethylorthoformate (20 mL). After addition of 2M HCl ether solution (1 mL), the resultant solution was heated at reflux for 3 h. Removal of solvents in vacuo afforded a protected aldehyde (XXIII) as a brown solid.

Method H: General Procedure to Introduce Alkyl Group (XXIV)

The resultant protected aldehyde (XXIII) was dissolved in anhydrous DMF (60 mL) and mixed with alkyl mesylate or alky bromide (2 to 3 equivalents), potassium iodide (1.5 equivalents) and potassium carbonate (1.5 equivalents). The reaction was stirred at 40° C. over 48 h. Then, the reaction mixture was diluted with water (200 mL), and the aqueous layer was extracted with EtOAc (80 mL×4). The combined organic layers were partitioned with water and brine, and dried over anhydrous MgSO$_4$, filtered, and solvent removed in vacuo. Purification by silica gel column chromatography, the product eluted with EtOAc/hexane (10% to 40%), afforded the desired protected aldehyde (XXIV) as a solid.

Method I: Deprotection of Aldehyde (XXV)

The solid (XXIV) was dissolved in acetone (25 mL) and treated with 2NHCl (8 mL) and stirred for 14 h. The acidic mixture was basified with saturated Na$_2$CO$_3$ (aq.). The aqueous layer was extracted with EtOAc (60 mL×4). The organic layers were combined and dried over anhydrous MgSO$_4$, filtered and solvent was removed in vacuo to give the desired product (XXV), which was used without further purification.

Example 2

Preparation of 3-Bromo-5-methylsulfanyl-2-(2-pyridin-3-yl-ethoxy)-benzaldehyde 3-Bromo-5-methylsulfanyl-2-(2-pyridin-3-yl-ethoxy)-benzaldehyde was prepared following the general procedures described in Methods G, H and I starting from compound XXII.

$^1$H NMR (400 MHz, CDCl$_3$) δ 10.07 (1H, s), 8.59 (1H, s), 8.53 (1H, m), 7.67-7.65 (2H, m), 7.59 (1H, m), 7.28-7.25 (1H, m), 4.23 (2H, t), 3.20 (2H, t), 2.49 (3H, s) ppm.

LC-MS (ES): found 352 (M+H)$^+$ and 354 (M+H)$^+$, as calculated: 351 for C$_{15}$H$_{14}$$^{79}$BrNO$_2$S and 353 for C$_{15}$H$_{14}$$^{81}$BrNO$_2$S.

Example 3

Preparation of 3-Bromo-5-methylsulfanyl-2-phenethyloxy-benzaldehyde

3-Bromo-5-methylsulfanyl-2-phenethyloxy-benzaldehyde was prepared following the general procedures described in Methods G, H and I, starting from compound XXII.

$^1$H NMR (400 MHz, CDCl$_3$) δ 10.0 (1H, s), 7.66 (1H, s), 7.58 (1H, s), 7.27 (5H, m), 4.25 (2H, t), 3.18 (2H, t), 2.49 (3H, s) ppm.

LC-MS (ES) found 351 (M+H)$^+$ and 353 (M+H)$^+$, as calculated: 350 for C$_{16}$H$_{15}$$^{79}$BrO$_2$S and 352 for C$_{16}$H$_{15}$$^{81}$BrO$_2$S.

Example 4

Preparation of 3-Bromo-5-methylsulfanyl-2-[2-(4-methyl-thiazol-5-yl)-ethoxy]-benzaldehyde 3-Bromo-5-methylsulfanyl-2-[2-(4-methyl-thiazol-5-yl)-ethoxy]-benzaldehyde was prepared following the general procedures described in Methods G, H and I, starting from compound XXII.

$^1$H NMR (400 MHz, CDCl$_3$) δ 10.13 (1H, s), 8.63 (1H, s), 7.66 (1H, d), 7.60 (1H, d), 4.19 (2H, t), 3.36 (2H, t), 2.49 (3H, s), 2.47 (3H, s).

LC-MS (ES): found 371 (M+H)$^+$ and 373 (M+H)$^+$, as calculated: 370 for $C_{14}H_{14}^{79}BrNO_2S_2$ and 372 for $C_{14}H_{14}^{81}BrNO_2S$

Example 5

Preparation of 5-{3-[3-Bromo-5-methylsulfanyl-2-(2-pyridin-3-yl-ethoxy)-benzylamino]-propylamino}-4H-thieno[3,2-b]pyridin-7-one. (Formula II)

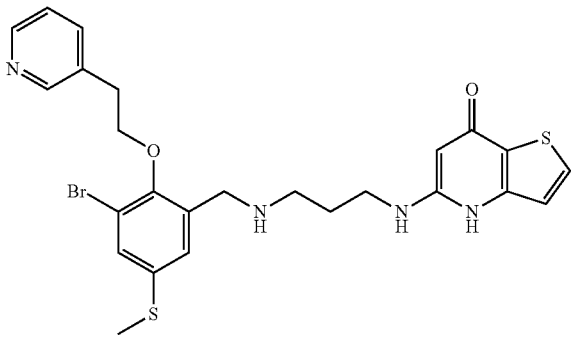 [SMILES: CSc1cc(Br)c(OCCc2cccnc2)c(CNCCCNc2cc(=O)c3sccc3[nH]2)c1]

5-{3-[3-Bromo-5-methylsulfanyl-2-(2-pyridin-3-yl-ethoxy)-benzylamino]-propylamino}-4H-thieno[3,2-b]pyridin-7-one was prepared by reductive amination of the aldehyde prepared in Example 2 with amine XVIII following method C, Scheme 1.

$^1$H NMR (400 MHz, CD$_3$OD) δ 8.51 (1H, s), 8.37 (1H, m), 7.78 (1H, d), 7.67 (1H, m), 7.34 (1H, s), 7.32 (1H, m), 7.23 (1H, s), 6.95 (1H, m), 5.56 (1H, s), 4.13 (2H, m), 3.53 (2H, s), 3.26-3.28 (4H, m), 3.11 (2H, m), 2.48 (2H, m), 2.42 (3H, s), 1.73 (2H, m).

LC-MS (ES): found 559 (M+H)$^+$, 561 (M+H)$^+$, and 557 (M−H)$^-$ and 559 (M−H)$^-$ as calculated: 558 for $C_{25}H_{27}^{79}BrN_4O_2S_2$ and 560 for $C_{25}H_{27}^{81}BrN_4O_2S_2$.

Example 6

Preparation of 5-(3-{3-bromo-5-methylsulfanyl-2-[2-(4-methyl-thiazol-5-yl)-ethoxy]-benzylamino}-propylamino)-4H-thieno[3,2-b]pyridine-7-one (Formula III)

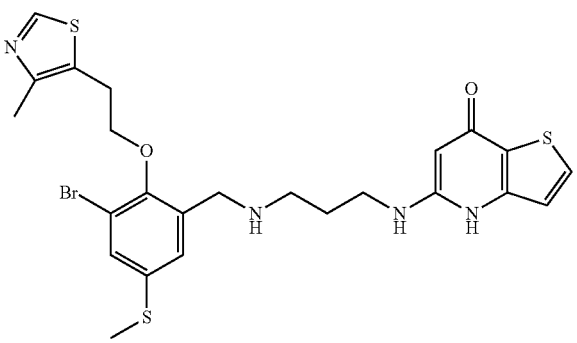 [SMILES: CSc1cc(Br)c(OCCc2scnc2C)c(CNCCCNc2cc(=O)c3sccc3[nH]2)c1]

5-(3-{3-bromo-5-methylsulfanyl-2-[2-(4-methyl-thiazol-5-yl)-ethoxy]-benzylamino}-propylamino)-4H-thieno[3,2-b]pyridine-7-one was prepared by reductive amination of the aldehyde prepared in Example 4 with amine XVIII following method C, Scheme 1. $^1$H NMR (400 MHz, CD$_3$OD) δ 8.75 (1H, s), 7.70 (1H, d), 7.41 (1H, s), 7.29 (1H, s), 6.98 (1H, d), 5.59 (1H, s), 4.13 (2H, t), 3.72 (2H, s), 3.33 (4H, m), 2.65 (2H, t), 2.46 (3H, s), 2.40 (3H, s), 1.73 (2H, d).

LC-MS (ES): found 579 (M+H)$^+$, 581 (M+H)$^+$, and 577 (M−H)$^-$ and 579 (M−H)$^-$ as calculated: 578 for $C_{24}H_{27}^{79}BrN_4O_2S_3$ and 580 for $C_{24}H_{27}^{79}BrN_4O_2S_3$.

Example 7

Preparation of 5-[3-(3-bromo-5-methylsulfanyl-2-phenethyloxy-benzylamino)-propylamino]-4H-thieno[3,2-b]pyridine-7-one (Formula IV)

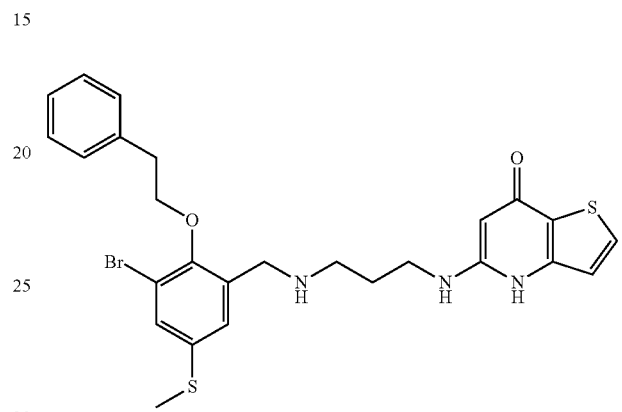

5-[3-(3-bromo-5-methylsulfanyl-2-phenethyloxy-benzylamino)-propylamino]-4H-thieno[3,2-b]pyridine-7-one was prepared by reductive amination of the aldehyde prepared in Example 3 with amine XVIII following method C.

$^1$H NMR (400 MHz, CD$_3$OD) δ 7.70 (1H, d), 7.41 (1H, s), 7.29 (1H, s), 7.25 (5H, m), 6.98 (1H, d), 5.59 (1H, s), 4.12 (2H, t), 3.72 (2H, s), 3.33 (4H, m), 2.65 (2H, t), 2.40 (3H, s), 1.73 (2H, d).

LC-MS (ES): found 558 (M+H)$^+$, 560 (M+H)$^+$, and 556 (M−H)$^-$ and 558 (M−H)$^-$ as calculated: 557 for $C_{26}H_{28}^{79}BrN_3O_2S_2$ and 559 for $C_{26}H_{28}^{81}BrN_3O_2S_2$.

Example 8

5-(3-{3,5-Dibromo-2-[2-(4-methyl-thiazol-5-yl)-ethoxy]-benzylamino}-propylamino)-4H-thieno[3,2-b]pyridin-7-one (Formula IV)

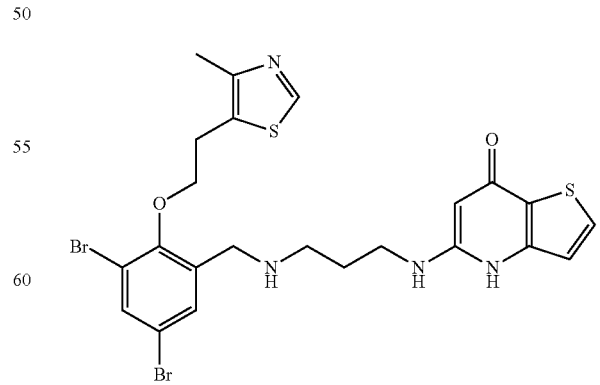

The aldehyde intermediate XVII was prepared via method A, followed by reductive amination (method B) with XVIII to give 5-(3-{3,5-Dibromo-2-[2-(4-methyl-thiazol-5-yl)-ethoxy]-benzylamino}-propylamino)-4H-thieno[3,2-b]pyridin-7-one.

¹H NMR (400 MHz, CD₃OD): δ 8.76 (s, 1H), 7.75 (d, 1H), 7.70 (d, 1H), 7.60 (d, 1H), 7.01 (d, 1H), 5.60 (s, 1H), 4.12 (t, 2H), 3.80 (s, 2H), 3.20-3.34 (m, 4H), 2.73 (t, 2H), 2.40 (s, 3H), 1.86 (m, 2H). MS (ES+): M/Z 612 (M+1).

Example 9

Preparation of 5-{3-[3,5-Dibromo-2-(2-pyridin-3-yl-ethoxy)-benzylamino]-propylamino}-4H-thieno[3,2-b]pyridin-7-one (Formula V)

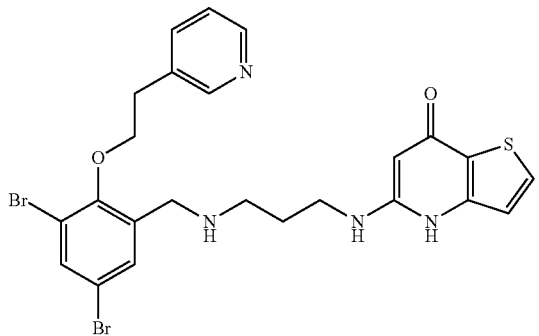 [SMILES: O=c1cc(NCCCNCc2cc(Br)cc(Br)c2OCCc2cccnc2)[nH]c2ccsc12]

The aldehyde intermediate XVII was prepared via method A, followed by reductive amination (method B) with XVIII to give 5-{3-[3,5-Dibromo-2-(2-pyridin-3-yl-ethoxy)-benzylamino]-propylamino}-4H-thieno[3,2-b]pyridin-7-one.

¹H NMR (400 MHz, CD₃OD): δ 8.54 (s, 1H), 8.41 (d, 1H), 7.84 (d, 1H), 7.82 (d, 1H), 7.73 (d, 1H), 7.69 (d, 1H), 7.39 (m, 1H), 7.10 (d, 1H), 5.64 (s, 1H), 4.23 (t, 2H), 4.04 (s, 2H), 3.38 (t, 2H), 3.20 (t, 2H), 2.98 (t, 2H), 1.99 (m, 2H). MS (ES+): M/Z 592 (M+1).

Example 10

Preparation of 5-(3-{3,5-Dibromo-2-[2-(4,5-dimethyl-thiazol-2-yl)-ethoxy]-benzylamino}-propylamino)-4H-thieno[3,2-b]pyridin-7-one (Formula VII)

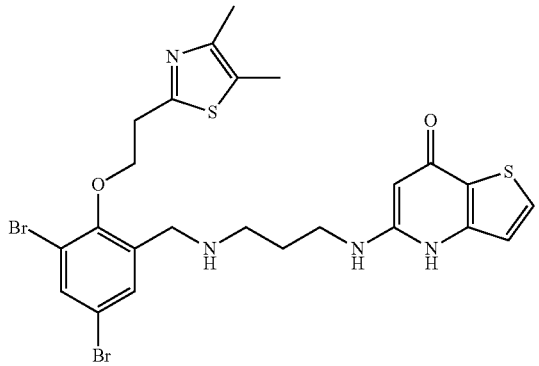 [SMILES: Cc1nc(CCOc2c(Br)cc(Br)cc2CNCCCNc2cc(=O)c3sccc3[nH]2)sc1C]

The aldehyde intermediate XVII was prepared via method A, followed by reductive amination (method B) with XVIII to give 5-(3-{3,5-Dibromo-2-[2-(4,5-dimethyl-thiazol-2-yl)-ethoxy]-benzylamino}-propylamino)-4H-thieno[3,2-b]pyridin-7-one.

¹H NMR (400 MHz, CD₃OD): δ 7.69 (d, 1H), 7.67 (d, 1H), 7.55 (d, 1H), 6.98 (d, 1H), 5.56 (s, 1H), 4.24 (t, 2H), 3.67 (s, 2H), 3.36 (t, 2H), 3.29 (t, 2H), 2.60 (t, 2H), 2.28 (s, 3H), 2.25 (s, 3H), 1.79 (m, 2H). MS (ES+): M/Z 626 (M+1).

Example 11

Preparation of 5-[3-(3,5-Dibromo-2-phenethyloxy-benzylamino)-propylamino]-4H-thieno[3,2-b]pyridin-7-one (Formula VIII)

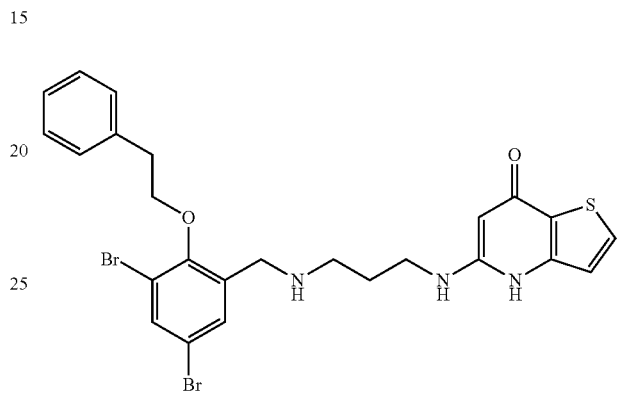

The aldehyde intermediate XVII was prepared via method A, followed by reductive amination (method B) with XVIII to give 5-[3-(3,5-Dibromo-2-phenethyloxy-benzylamino)-propylamino]-4H-thieno[3,2-b]pyridin-7-one.

¹H NMR (400 MHz, CD₃OD): δ 7.69 (d, 1H), 7.65 (d, 1H), 7.50 (d, 1H), 7.29-7.20 (m, 4H), 7.18-7.12 (m, 1H), 6.98 (d, 1H), 5.57 (s, 1H), 4.14 (t, 2H), 3.51 (t, 2H), 3.26 (t, 2H), 3.06 (t, 2H), 2.44 (t, 2H), 1.70 (m, 2H). MS (ES+): M/Z 592 (M+1).

Example 12

Preparation of 5-{3-[3,5-Dibromo-2-(3-pyridin-3-yl-propoxy)-benzylamino]-propylamino}-4H-thieno[3,2-b]pyridin-7-one (Formula IX)

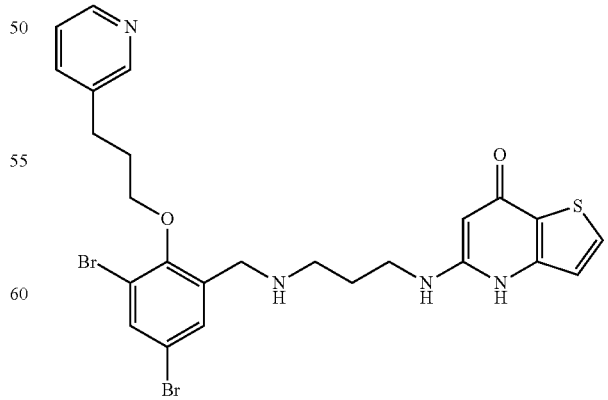

The aldehyde intermediate XVII was prepared via method A, followed by reductive amination (method B) with XVIII to give 5-{3-[3,5-Dibromo-2-(3-pyridin-3-yl-propoxy)-benzylamino]-propylamino}-4H-thieno[3,2-b]pyridin-7-one.

$^1$H NMR (400 MHz, CD$_3$OD): δ8.43 (s, 1H), 8.35 (d, 1H), 7.73-7.64 (m, 3H), 7.58 (s, 1H), 7.34 (t, 1H), 7.00 (d, 1H), 5.56 (s, 1H), 3.95 (t, 2H), 3.81 (s, 2H), 3.32 (t, 2H), 2.87 (t, 2H), 2.69 (t, 2H), 2.12 (m, 2H), 1.85 (m, 2H). MS (ES+): M/Z 607 (M+1).

Example 13

Preparation of 5-(3-{3,5-Dibromo-2-[2-(3,4-dichloro-phenyl)-ethoxy]-benzylamino}-propylamino)-4H-thieno[3,2-b]pyridin-7-one (Formula X)

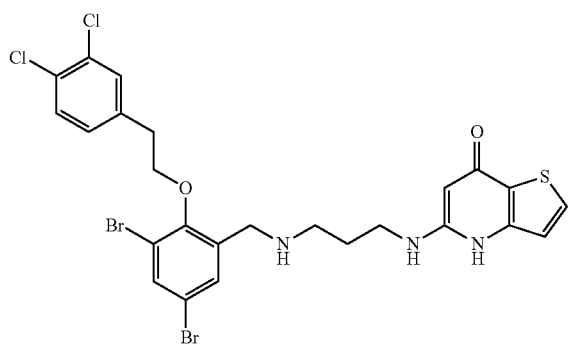 [SMILES: O=c1cc(NCCCNCc2cc(Br)cc(Br)c2OCCc2ccc(Cl)c(Cl)c2)[nH]c2ccsc12]

The aldehyde intermediate XVII was prepared via method A, followed by reductive amination (method B) with XVIII to give 5-(3-{3,5-Dibromo-2-[2-(3,4-dichloro-phenyl)-ethoxy]-benzylamino}-propylamino)-4H-thieno[3,2-b]pyridin-7-one.

$^1$H NMR (400 MHz, DMSO-d$_6$): δ7.70 (s, 1H), 7.68 (d, 1H), 7.61 (d, 2H), 7.54 (d, 1H), 7.31 (d, 1H), 7.04 (d, 1H), 6.30 (br s, 1H), 4.08 (t, 2H), 3.47 (s, 2H), 3.26-3.12 (m, 2H), 3.05 (t, 2H), 2.45 (t, 2H), 1.64 (m, 2H). MS (ES+): M/Z 660, 662 (M+1).

Example 14

Preparation of 5-(3-{3,5-Dibromo-2-[2-(4-methoxy-phenyl)-ethoxy]-benzylamino}-propylamino)-4H-thieno[3,2-b]pyridin-7-one (Formula XI)

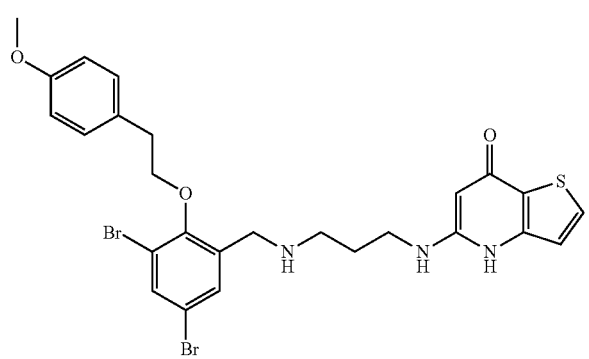 [SMILES: COc1ccc(CCOc2c(Br)cc(Br)cc2CNCCCNc2cc(=O)c3sccc3[nH]2)cc1]

The aldehyde intermediate XVII was prepared via method A, followed by reductive amination (method B) with XVIII to give 5-(3-{3,5-Dibromo-2-[2-(4-methoxy-phenyl)-ethoxy]-benzylamino}-propylamino)-4H-thieno[3,2-b]pyridin-7-one.

$^1$H NMR (400 MHz, CD$_3$OD): δ 7.69 (d, 1H), 7.66 (s, 1H), 7.50 (s, 1H), 7.17 (d, 2H), 6.96 (d, 1H), 6.81 (d, 2H), 5.57 (s, 1H), 4.10 (t, 2H), 3.69 (s, 3H), 3.50 (s, 2H), 3.25 (t, 2H), 3.00 (t, 2H), 2.45 (t, 2H), 1.70 (m, 2H). MS (ES+): M/Z 622 (M+1).

Example 15

Preparation of 5-{3-[3,5-Dibromo-2-(2-p-tolyl-ethoxy)-benzylamino]-propylamino}-4H-thieno[3,2-b]pyridin-7-one (Formula XII)

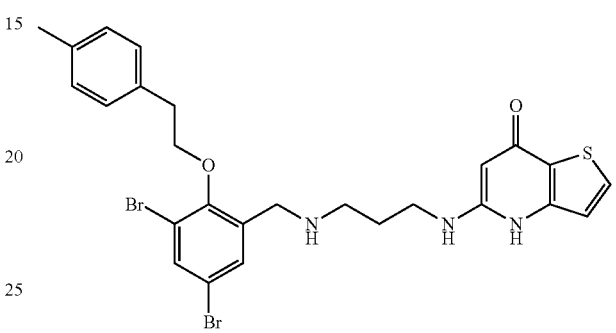

The aldehyde intermediate XVII was prepared via method A, followed by reductive amination (method B) with XVIII to give 5-{3-[3,5-Dibromo-2-(2-p-tolyl-ethoxy)-benzylamino]-propylamino}-4H-thieno[3,2-b]pyridin-7-one.

$^1$H NMR (400 MHz, DMSO-d$_6$): δ 7.72 (s, 1H), 7.69 (d, 1H), 7.60 (s, 1H), 7.16 (d, 2H), 7.08 (d, 2H), 7.04 (d, 1H), 6.32 (br, s, 1H), 4.05 (t, 2H), 3.53 (s, 2H), 3.26-3.14 (m, 2H), 2.99 (t, 2H), 2.46 (t, 2H), 2.24 (s, 3H), 1.64 (m, 2H). MS (ES+): M/Z 606 (M+1).

Example 16

Preparation of 5-(3-{3,5-Dibromo-2-[2-(3-fluoro-phenyl)-ethoxy]-benzylamino}-propylamino)-4H-thieno[3,2-b]pyridin-7-one (Formula XIII)

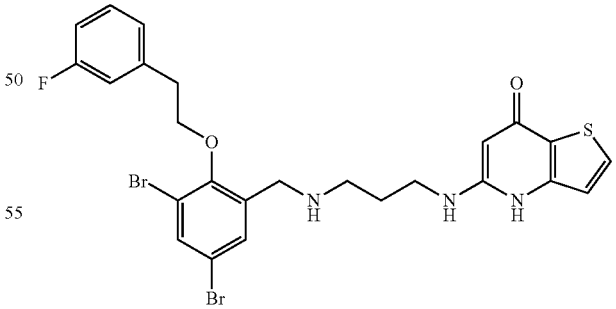

The aldehyde intermediate XVII was prepared via method A, followed by reductive amination (method B) with XVIII to give 5-(3-{3,5-Dibromo-2-[2-(3-fluoro-phenyl)-ethoxy]-benzylamino}-propylamino)-4H-thieno[3,2-b]pyridin-7-one.

$^1$H NMR (400 MHz, DMSO-d$_6$): δ7.69 (d, 1H), 7.66 (s, 1H), 7.52 (s, 1H), 7.25 (q, 1H), 7.12-7.04 (m, 2H), 6.99 (d,

2H), 6.90 (t, 1H), 5.57 (s, 1H), 4.14 (t, 2H), 3.55 (s, 2H), 3.26 (t, 2H), 3.09 (t, 2H), 2.49 (t, 2H), 1.73 (m, 2H). MS (ES+): M/Z 610 (M+1).

Example 17

Preparation of 5-(3-{3,5-Dibromo-2-[2-(4-chlorophenyl)-ethoxy]-benzylamino}-propylamino)-4H-thieno[3,2-b]pyridin-7-one (Formula XIV)

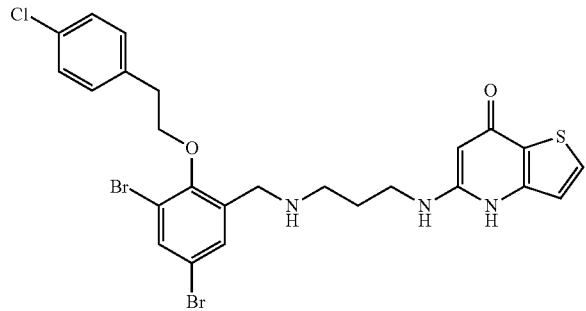 [SMILES: O=c1cc(NCCCNCc2cc(Br)cc(Br)c2OCCc2ccc(Cl)cc2)[nH]c2ccsc12]

The aldehyde intermediate XVII was prepared via method A, followed by reductive amination (method B) with XVIII to give 5-(3-{3,5-Dibromo-2-[2-(4-chloro-phenyl)-ethoxy]-benzylamino}-propylamino)-4H-thieno[3,2-b]pyridin-7-one.

$^1$H NMR (400 MHz, DMSO-d$_6$): δ7.70 (s, 1H), 7.69 (d, 1H), 7.60 (s, 1H), 7.33 (s, 4H), 7.04 (d, 1H), 6.31 (br, s, 1H), 4.07 (t, 2H), 3.49 (s, 2H), 3.26-3.15 (m, 2H), 3.03 (t, 2H), 2.45 (t, 2H), 1.64 (m, 2H). MS (ES+): M/Z 626 (M+1).

Example 18

Preparation of 5-{3-[3-Bromo-5-methylsulfanyl-2-(3-pyridin-3-yl-propoxy)-benzylamino]-propylamino}-4H-thieno[3,2-b]pyridin-7-one (Formula XV)

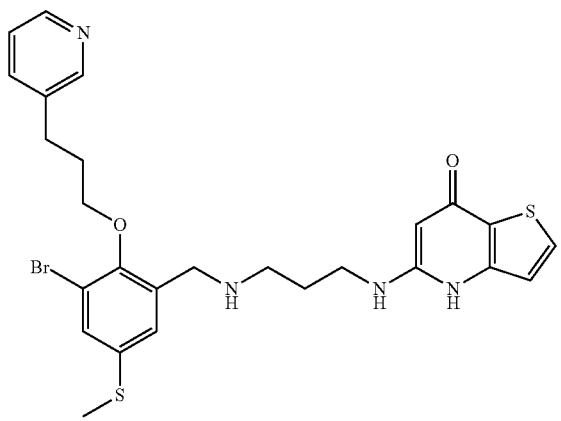 [SMILES: CSc1cc(Br)c(OCCCc2cccnc2)c(CNCCCNc2cc(=O)c3sccc3[nH]2)c1]

The aldehyde intermediate XVII was prepared via method A, followed by reductive amination (method B) with XVIII to give 5-{3-[3-Bromo-5-methylsulfanyl-2-(3-pyridin-3-yl-propoxy)-benzylamino]-propylamino}-4H-thieno[3,2-b]pyridin-7-one.

$^1$H NMR (400 MHz, CD$_3$OD): δ 8.42 (s, 1H), 8.33 (d, 1H), 7.72-7.64 (m, 2H), 7.38-7.27 (m, 3H), 6.97 (d, 1H), 5.55 (s, 1H), 3.93 (t, 2H), 3.80 (s, 2H), 3.32 (t, 2H), 2.87 (t, 2H), 2.70 (t, 2H), 2.43 (s, 3H), 2.11 (m, 2H), 1.84 (m, 2H). MS (ES+): M/Z 574.7 (M+1).

Example 19

Expression and Purification of MetRS

The following example illustrates expression and purification of *C. difficile* MetRS useful in the functional assays shown in Examples 20, 21, and 22.

Cloning of Over-Producing Vector:

N-terminally hexaHis-tagged *C. difficile* MetRS was amplified and cloned into pETcoco-2. The following primers were used to amplify DNA from genomic DNA: 5'-CTGCA-GAGCTAGCAAACCGAGTTTTTATGTAAC-3' (forward) (SEQ ID NO:1), 5'-CTTTCTAAGCTTCTACTAACGAAC-CTCGGATCC-3' (reverse) (SEQ ID NO:2). Amplified DNA was treated with Sph1 and HindIII restriction endonucleases, which were heat-inactivated after digestion. The fragment was ethanol-precipitated and combined with pETcoco-2 vector (Novagen) that had been treated with the same enzymes plus shrimp alkaline phophatase. The fragments were ligated and the ligation mixture transformed into competent DH10 *E. coli*. Transformants were plated on F-medium plus glucose with 50 ug/ml ampicillin. Growth in glucose maintains the repressed state of the pBAD promoter driving expression of the replicator TrfA, thus maintaining low copy number. The resulting expression clone, pETcoco-Cdiff-MRS, was confirmed by sequencing of the insert in both directions.

Purification of *C. difficile* MetRS.

The expression vector pETcoco-Cdiff-MRS was transformed into Rosetta DE3 expression strain and used to inoculate 4 liters of F media supplemented with 10 ug/mL chloramphenicol, 50 ug/mL ampicillin, 0.2% glucose. The culture was induced with 1 mM IPTG at OD 0.66. Cells were harvested 4 hours post-induction (yield=38 g cell pellet). Pelleted cells were lysed by adding 78 g of a 1:1 suspension of frozen cells (39 g cells) in Tris-sucrose which had been stored at −20° C. to 107.25 ml Tris-sucrose buffer that had been pre-warmed to 45° C. (2.75 ml/g of cells). To the stirred mixture, 1.95 ml of 0.5M 1,4-dithiothreitol (DTT) (0.05 ml/g of cells) and 9.75 ml of lysis buffer (2M NaCl, 0.3M spermidine in Tris-sucrose adjusted to pH 7.5) (0.25 ml/g of cells) was added. The pH of the slurry was tested with pH paper and adjusted to pH 8.0 by the addition of 50 ml of 2 M Tris base. Lysozyme (117 mg) was added in 20 ml of Tris-sucrose buffer (3 mg lysozyme/g of cells). The slurry was distributed into centrifuge bottles and incubated at 4° C. for 1 hour followed by incubation at 37° C. for 4 minutes. The insoluble cellular components were removed by centrifugation (23,000×g, 60 min, 4° C.). The recovered supernatant (192 ml) constituted Fraction I. Fraction I was loaded onto a 15 mL Ni-NTA column which was equilibrated in Load Buffer (50 mM Tris-HCl, pH 7.5, 10% glycerol, 40 mM KCl, 10 mM imidazole, pH 6.8, and 7 mM beta mercaptoethanol). The column was washed with 10 column volumes of Wash Buffer (50 mM Tris-HCl, pH 7.5, 10% glycerol, 800 mM KCl, 20 mM Imidazole, pH 6.8, and 7 mM beta mercaptoethanol). The protein was eluted in 10 column volume gradient from Wash Buffer to Elution Buffer (50 mM Tris-HCl, pH 7.5, 10% glycerol, 40 mM KCl, 250 mM Imidazole, pH 6.8, and 7 mM beta mercaptoethanol) at 0.5 mL/min collecting 3 mL fractions. Fractions were collected and analyzed for protein by SDS-PAGE. Fractions were assayed in the *C. difficile* MetRS tRNA charging assay. Fractions containing peak activity were pooled to form Fraction II (60 mg at 1.3 mg/ml). Fraction II had a specific activity of $3.2 \times 10^5$ units per mg. The purity was estimated at greater than 97% based on densitometry of an SDS-PAGE gel stained with Coomassie blue.

Example 20

Compounds of the Present Invention have Potent Enzyme Activity Against MetRS Compounds of the present invention were assayed to determine their ability to inhibit enzyme MetRS. Assays were performed as follows:

| Reaction Mix (per 1 ml) | | |
| --- | --- | --- |
| Stock | Volume (μl) | Final Concentration |
| 100 mM Tris/Cl, pH 7.9 | 600 | 30 mM |
| 250 mM KCl | | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 20 | 10 μM |
| Solid tRNA (Mixed E. coli MRE 600) | 4 mg/ml | 2 mg/ml |
| H$_2$O | 180 | |
| 10 x Inhibitor (0-100 μM) 5 μl per well | 0-10 μM | |

Each reaction was started by adding 20 μl appropriately diluted pure enzyme (pre-incubated with inhibitor) to 25 μl reaction mix for 10 min at room temperature. The reaction is terminated by the addition of 150 μl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed E. coli MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Sigma.

Results

Compounds having formulas (II)-(XV) had IC$_{50}$ values against C. difficile MetRS in the range <1.5-15 nM. All were highly selective with respect to the mammalian enzyme (no inhibition of rat MetRS up to 1 μM). This data indicates that the compounds of the present invention show strong selectivity toward inhibition of C. difficile MetRS, but have little or no inhibitory activity toward mammalian MetRS. MetRS inhibitor compounds are competitive inhibitors of methionine and uncompetitive inhibitors of ATP.

Example 21

Compounds of the Present Invention have Potent Antibacterial Activity Against C. difficile Compounds (formulas (II)-(XV)) of the present invention were also assayed for their capacity to inhibit C. difficile growth. MIC$_{90}$ (minimum inhibition concentration required to inhibit the growth of 90% of C. difficile) was determined using standard agar based assays according to CLSI.

Organisms:

All compounds were tested for antibacterial activity against a collection of non-repeat clinical isolates of C. difficile. The organisms were stored frozen in Brucella broth supplemented with 20% glycerol. The organisms were retrieved from the freezer and subcultured twice onto CDC agar to ensure purity and growth. The plates were incubated under anaerobic conditions for at least 24 hours. Bacterial colonies were examined for morphology; yellow color, ground glass texture and characteristic odor. The control organism tested was Bacteroides fragilis ATCC 25285.

Antimicrobial Susceptibility Testing:

Antimicrobial susceptibility testing was conducted by the agar dilution method on Brucella agar supplemented with vitamin K$_1$, hemin and 5% laked sheep blood in accordance with CLSI guidelines (CLSI, M11-A2). The test compounds were serially diluted and added to molten supplemented Brucella agar. Drug free plates were inoculated before and after inoculation of each antimicrobial plate series and were used as growth controls. Anaerobic/aerobic growth controls were conducted on drug free plates after two sets of drug plates. Bacterial colonies were suspended in Brucella broth to a turbidity equal to that of a 0.5 McFarland standard and applied to a plate with a Steers replicator that delivered 10$^5$ CFU/spot. The plates were incubated under anaerobic conditions for 24 hours at 35° C. prior to the reading of the results. The minimum inhibitory concentration (MIC) was the concentration that completely inhibited growth or caused a marked reduction in the appearance of growth compared to that of the drug-free growth control.

Results:

Data from the present example shows MIC$_{90}$ for formulas (II) to (XV) which ranged from 0.5 to >32 μg/ml. These results indicate the potent activity of the compounds of the present invention against C. difficile, typically around 1.0 μg/ml. In addition, IC$_{50}$ data indicates that the compounds of the present invention are specific for C. difficile, showing little or no activity against mammalian MetRS. MetRS inhibitor compounds show potent activity against C. difficile and Gram-positive aerobic bacteria while sparing normal gut flora.

Example 22

Compounds of the Present Invention have Potent Antibacterial Activity Against Other Bacteria Several compounds (formulas (II), (III) and (IV)+others (all were tested) of the present invention were tested for antibacterial activity against a panel of Gram-positive bacteria. Compounds were tested against Gram-positive aerobic bacteria using the CLSI-reference broth microdilution method. Data was obtained against S. aureus, E. faecalis, E. faecium, S. pyogenes, S. epidermis and S. haemolyticus. The compounds tested demonstrated potent antibacterial activity against all isolates with a MIC range of <0.008-8 μg/ml, including resistant strains of S. aureus, S. epidermidis and S. pyogenes. Data was also obtained against Helicobacter, H. pylori using the standard CLSI guideline agar dilution method and results indicate that the compounds of the invention are active against H. pylori.

The data illustrated the utility of using the compounds of the present invention as antibacterial agents against other Gram-positive bacteria, e.g., S. aureus, E. faecalis, E.

faecium, S. pyogenes, S. epidermidis, and S. haemolyticus, and against the Gram-negative bacteria H. pylori.

Example 23

Compounds of the Present Invention Show Strong Therapeutic Utility During In Vivo Trials Animal studies were performed to determine the efficacy of MetRS inhibitors for treating C. difficile-infections. The MetRS inhibitors tested were 5-[3-((R)-6,8-Dibromo-chroman-4-ylamino)-propylamino]-4H-thieno[3,2-b]pyridine-7-one (both racemic mixture and the R enantiomer), 5-[3-((R)-8-Bromo-6-chloro-chroman-4-ylamino)-propylamino]-4H-thieno[3,2-b]pyridin-7-one, and 2-(3-{3,5-Dibromo-2-[2-(4-methyl-thiazol-5-yl)-ethoxy]-benzylamino}-propylamino)-1H-quinolin-4-one.

Results were compared to C. difficile-infected hamsters treated with the conventional antibiotic, vancomycin. Infected hamsters were treated with either a solution or suspension of a MetRS inhibitor at 5 to 50 mg/kg or vancomycin at 2.5, 5 or 25 mg/kg. There were eight hamsters per group with the final endpoint of the experiment being survival. Expired hamsters were examined for GI condition.

Data for the studies indicated that control hamsters (infected with C. difficile but receiving no treatment) died within 3-4 days. Hamsters treated with MetRS inhibitors showed a significant increase in survival, often living until study termination, typically 28 or more days. These results were similar or superior to the results obtained using vancomycin treatment. 5-[3-((R)-6,8-Dibromo-chroman-4-ylamino)-propylamino]-4H-thieno[3,2-b]pyridine-7-one demonstrated the best efficacy. 5-[3-((R)-6,8-Dibromo-chroman-4-ylamino)-propylamino]-4H-thieno[3,2-b]pyridine-7-one exhibited superior efficacy to vancomycin in that >60% survival was observed on Day 28 (5 mg/kg BID) as compared to 0-10% survival with vancomycin. Surviving animals had healthy GI appearance and histopathology. Low systemic exposure and bioavailability was observed in hamsters following oral administration of the MetRS inhibitors.

The data in this Example illustrates that the compounds of the present invention were comparable or superior to vancomycin in their capability to treat animals infected with C. difficile.

Example 24

Compounds of the Present Invention Effect Toxin Production in C. difficile

The pathogenicity of C. difficile is associated with its ability to produce the extracellular toxins A and B. Hypertoxinogenic strains are responsible for recent outbreaks with high mortality. In contrast, isolates that do not produce toxins are non-pathogenic. Since toxin production requires active protein synthesis, inhibition of the protein synthesis machinery is expected to suppress de novo toxin production. Therefore, MetRS inhibitors were evaluated for their effect on C. difficile toxin production in vitro.

Methods:

C. difficile strain ATCC43255 was grown and maintained anaerobically on CDC anaerobe agar (Remel, Lenexa, Kans.). To test the effect of antibacterial agents on growth, cells were grown anaerobically for 40 h at 35° C. in 96-well brain heart infusion (BHI) broth cultures, with an initial inoculum of $10^6$ CFU/mL. To test the effect of antibacterial agents on toxin production at high C. difficile cell densities, the cells were grown anaerobically for 24 h at 35° C. in 96-well brain heart infusion (BHI) broth cultures. Spent medium was then replaced with fresh broth containing MetRS inhibitors and control agents at a concentration range of 0.015-16 μg/mL. After 4 days, growth and cell viability were monitored by optical density measurements at 595 nm and by culture on CDC anaerobe agar, respectively. Culture supernatants were collected, and toxin A was detected by ELIFA (enzyme-linked immuno-flow assay) using an anti toxin A monoclonal antibody (Novus Biologicals, Centennial, Colo.).

Results:

The MetRS inhibitors 5-[3-(6,8-Dibromo-chroman-4-ylamino)-propylamino]-4H-thieno[3,2-b]pyridin-7-one and 5-(3-{3,5-Dibromo-2-[2-(4-methyl-thiazol-5-yl)-ethoxy]-benzylamino}-propylamino)-4H-thieno[3,2-b]pyridin-7-one prevented growth of C. difficile in broth at concentrations of ≥0.25 μg/mL.

Toxin production in high cell density, 4 day old stationary phase cultures was inhibited by four different MetRS inhibitors (5-[3-(6,8-Dibromo-chroman-4-ylamino)-propylamino]-4H-thieno[3,2-b]pyridin-7-one, 5-(3-{3,5-Dibromo-2-[2-(4-methyl-thiazol-5-yl)-ethoxy]-benzylamino}-propylamino)-4H-thieno[3,2-b]pyridin-7-one, R-(+)-5-[3-(6,8-Dibromo-chroman-4-ylamino)-propylamino]-4H-thieno[3,2-b]pyridin-7-one di-hydrochloride, 5-[3-(6,8-Dibromo-1,2,3,4-tetrahydro-quinolin-4-ylamino)-propylamino]-4H-thieno[3,2-b]pyridin-7-one tri-hydrochloride) at concentrations as low as 0.25 μg/mL. In contrast, much higher concentrations (4->16 μg/mL) of the comparator agents (metronidazole, vancomycin, levofloxacin) were required to inhibit toxin production.

CONCLUSIONS

MetRS inhibitors demonstrate inhibitory effects on both growth and toxin production of C. difficile in broth cultures. Furthermore, toxin production was effectively blocked in stationary phase cultures. As a consequence of this suppression of toxin production by bacteriostatic MetRS inhibitors, C. difficile becomes essentially non-toxinogenic and thus non-pathogenic. This effect is unique to protein synthesis inhibitors, such as MetRS inhibitors, whose mode-of-action does not require that the bacteria are actively growing.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A compound of formula (I):

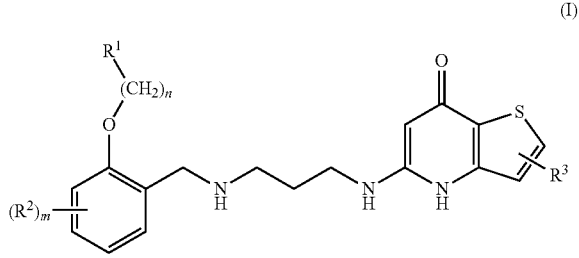

in which:
R[1] is selected from the group consisting of aryl and heteroaryl groups, including but not limited to substituted and unsubstituted benzene, toluene, phenol, anisole, thiazole, thiazolidine and pyridine, alkenes, imines, and other like substituents;

$R^2$ is independently selected from halo, cyano, hydroxyl, $(C_{1-6})$alkyl (optionally substituted by halo, hydroxyl, amino, carboxy, or $(C_{1-6})$ alkoxycarbonyl), $(C_{1-6})$ cycloalkyl, $(C_{1-6})$ alkoxy, amino, mono- or di-$(C_{1-6})$ alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heteroxy;

$R^3$ is selected from a halo, $(C_{1-3})$alkyl, $(C_{2-3})$alkenyl, $(C_{2-3})$alkynyl or other like substituents;

n is one, two or three; and m is 0 or an integer from 1 to 3.

2. The compound of claim 1 having a formula (IA):

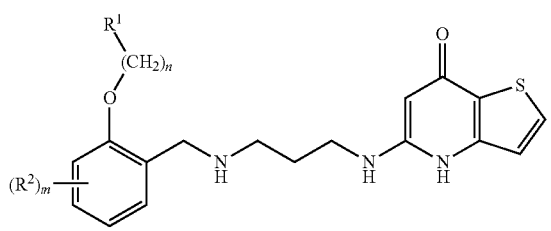

(IA)

in which:

$R^1$ is selected from the group consisting of substituted and unsubstituted benzene, such as toluene, phenol, anisole, substituted and unsubstituted thiazole, such as methylthiazole, substituted and unsubstituted pyridine, and alkenyl groups ethanimine, and $(C_1-C_6)$alkene; and $R^2$ is one or more halogen substituents (preferably bromine, iodine and/or chlorine), one or more sulfane substituents, e.g., methylsulfane, or a combination of a halogen and sulfane substituents.

3. The salt of the compound of claim 1.

4. The salt of claim 3 wherein the salt is a pharmaceutically acceptable salt.

5. A compound of formula (I) as claimed in claim 1 selected from:

5-{3-[3-Bromo-5-methylsulfanyl-2-(2-pyridin-3-yl-ethoxy)-benzylamino]-propylamino}-4H-thieno[3,2-b]pyridine-7-one;

5-(3-{3-bromo-5-methylsulfanyl-2-[2-(4-methyl-thiazol-5-yl)-ethoxyl]-benzylamino}-propylamino)-4H-thieno[3,2-b]pyridine-7-one;

5-[3-(3-bromo-5-methylsulfanyl-2-phenethyloxy-benzylamino)-propylamino]-4H-thieno[3,2-b]pyridine-7-one;

5-(3-{3,5-Dibromo-2-[2-(4-methyl-thiazol-5-yl)-ethoxyl]-benzylamino}-propylamino)-4H-thieno[3,2-b]pyridine-7-one;

5-{3-[3,5-Dibromo-2-(2-pyridin-3-yl-ethoxy)-benzylamino]-propylamino}-4H-thieno[3,2-b]pyridine-7-one;

5-(3-{3,5-Dibromo-2-[2-(4,5-dimethyl-thiazol-2-yl)-ethoxy]-benzylamino}-propylamino)-4H-thieno[3,2-b]pyridine-7-one;

5-[3-(3,5-Dibromo-2-phenethyloxy-benzylamino)-propylamino]-4H-thieno[3,2-b]pyridine-7-one;

5-{3-[3,5-Dibromo-2-(3-pyridin-3-yl-propoxy)-benzylamino]-propylamino}-4H-thieno[3,2-b]pyridine-7-one;

5-(3-{3,5-Dibromo-2-[2-(3,4-dichloro-phenyl)-ethoxy]-benzylamino}-propylamino)-4H-thieno[3,2-b]pyridine-7-one;

5-(3-{3,5-Dibromo-2-[2-(4-methoxy-phenyl)-ethoxy]-benzylamino}-propylamino)-4H-thieno[3,2-b]pyridine-7-one;

5-{3-[3,5-Dibromo-2-(2-p-tolyl-ethoxy)-benzylamino]-propylamino}-4H-thieno[3,2-b]pyridine-7-one;

5-3-{3,5-Dibromo-2-[2-(fluoro-phenyl)-ethoxy]-benzylamino}-propylamino)-4H-thieno[3,2-b]pyridine-7-one;

5-(3-{3,5-Dibromo-2-[2-(4-chloro-phenyl)-ethoxy]-benzylamino}-propylamino)-4Hthieno[3,2-b]pyridine-7-one; and 5-{3-[3-Bromo-5-methylsulfanyl-2-(3-pyridin-3-yl-propoxy)-benzylamino]-propylamino}-4H-thieno[3,2-b]pyridine-7-one.

6. A pharmaceutical composition comprising an antibacterially effective amount of a compound according to claim 1 together with a pharmaceutically accepted carrier or excipient.

7. A process for preparing a compound of formula (IA), according to claim 2, which process comprises reacting a compound of formula XVII:

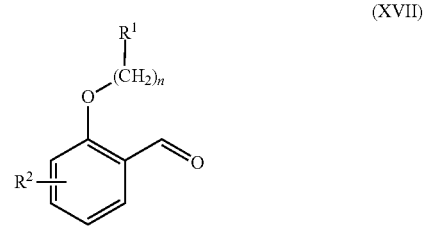

(XVII)

in which $R^1$ and $R^2$ are as defined in claim 1; with a compound of formula (XVIII):

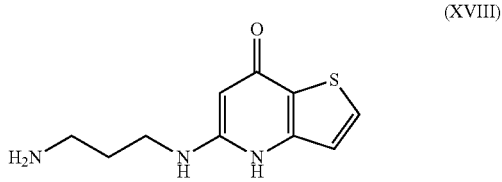 [SMILES: NCCCNc1cc(=O)c2sccc2[nH]1]

(XVIII)

under reductive amination conditions.

* * * * *